(12) United States Patent
Saito (10) Patent No.: US 8,187,244 B2
(45) Date of Patent: May 29, 2012

(54) UNDERPANTS TYPE DISPOSABLE DIAPER

(75) Inventor: Tetsuhiro Saito, Sakura (JP)

(73) Assignee: Daio Paper Corporation, Ehime (JP)

( * ) Notice: Subject to any disclaimer, the term of this patent is extended or adjusted under 35 U.S.C. 154(b) by 400 days.

(21) Appl. No.: 12/311,449

(22) PCT Filed: Sep. 28, 2007

(86) PCT No.: PCT/JP2007/069018
§ 371 (c)(1),
(2), (4) Date: Mar. 27, 2009

(87) PCT Pub. No.: WO2008/041640
PCT Pub. Date: Apr. 10, 2008

(65) Prior Publication Data
US 2009/0281512 A1   Nov. 12, 2009

(30) Foreign Application Priority Data

Sep. 29, 2006   (JP) .................................. 2006-269672

(51) Int. Cl.
*A61F 13/15* (2006.01)
(52) U.S. Cl. .................... 604/385.31; 604/365; 604/396
(58) Field of Classification Search ............ 604/385.31, 604/396, 365, 394
See application file for complete search history.

(56) References Cited

U.S. PATENT DOCUMENTS

| | | | | |
|---|---|---|---|---|
| 5,749,865 A | * | 5/1998 | Yamamoto et al. | 604/385.29 |
| 5,931,827 A | * | 8/1999 | Buell et al. | 604/385.29 |
| 6,394,991 B1 | * | 5/2002 | Takei et al. | 604/396 |
| 6,454,747 B1 | * | 9/2002 | Shimada et al. | 604/312 |
| 6,840,930 B1 | * | 1/2005 | Miyamoto et al. | 604/385.31 |
| 2002/0165514 A1 | * | 11/2002 | Datta et al. | 604/385.11 |
| 2003/0216706 A1 | * | 11/2003 | Olsson et al. | 604/387 |

FOREIGN PATENT DOCUMENTS

| | | |
|---|---|---|
| GB | 2 257 652 A | 1/1993 |
| JP | H07-75653 A | 3/1995 |
| JP | H7-34814 | 6/1995 |
| JP | H9-287 | 5/1997 |
| JP | H9-238980 | 9/1997 |
| JP | 3045174 | 1/1998 |
| JP | H10-52458 | 2/1998 |
| JP | H10-137288 | 5/1998 |
| JP | 2001-178770 | 7/2001 |
| JP | 2001-314441 | 11/2001 |
| JP | 2002-291801 | 10/2002 |
| JP | 2003-24383 | 1/2003 |
| JP | 2005-211179 A | 8/2005 |
| JP | 2006-006780 | 1/2006 |
| WO | WO 97/30671 A | 8/1997 |
| WO | WO 02/17843 A | 3/2002 |

* cited by examiner

*Primary Examiner* — Lynne Anderson
*Assistant Examiner* — Peter S Vasat
(74) *Attorney, Agent, or Firm* — DLA Piper LLP (US)

(57) ABSTRACT

[Problem] To eliminate a hardened portion from each joined section of an underpants type disposable diaper.

[Means for Solving Problem] An underpants type disposable diaper wherein a large number of unit fusing portions are arranged at uniform intervals along the longitudinal direction of each joined section and the joined section is divided into segments having different numbers of laminated sheets and different heights of unit fusing portions.

8 Claims, 7 Drawing Sheets

UNDERPANTS TYPE DISPOSABLE DIAPER

TECHNICAL FIELD

The present invention relates to an underpants type disposable diaper, and more specifically to an underpants type disposable diaper that can be treated after the usage and has a waist opening and a pair of right and left leg openings which are formed by joining a front body part and a back body part at both side edges.

BACKGROUND ART

An underpants type disposable diaper is folded at a crotch portion so that a front body part and a back body part are overlapped, and then joined at opposite edges on both sides in a longitudinal direction, thereby to form a waist opening and a pair of right and left leg openings. Resilient and elastic members are arranged as appropriate along the waist opening and the leg openings so as to fit the diaper to the body of a wearer.

In addition, an underpants type disposable diaper has a basic layered structure with a liquid permeable face sheet, a liquid impermeable back sheet, and an absorber between the two sheets, and also has a lamination structure with an additional leak prevention sheet and the like arranged at appropriate positions.

In a particularly employed lamination structure, a larger number of sheets are arranged around the waist opening, such as a back leak prevention sheet and a reinforcing sheet for example, whereas a smaller number of sheets are arranged around the leg openings not so as to interfere with movement of the legs of a wearer.

Therefore, in many cases, an underpants type disposable diaper varies in number of laminated sheets partially at the joined sections.

Furthermore, in many cases, even an underpants type disposable diaper with no layered structure at the joined sections may vary in density of arranged resilient and elastic members around the waist opening and the leg openings, which makes differences in required adhesion force.

Patent Document 1: JP 2002-291801 A
Patent Document 2: JP 2001-178770 A

DISCLOSURE OF THE INVENTION

Technical Problems to be Solved

However, a conventional underpants type disposable diaper is thermally fused at the joined sections in a uniform manner with reference to a portion requiring a largest joint strength, regardless partial differences in number of laminated sheets at the joined sections. Therefore, the diaper becomes hardened at portions with relatively smaller number of laminated sheets or with smaller densities of resilient and elastic members, such as portions of the joined sections adjacent to the side edges of the leg openings. In many cases, this leads to a problem that the hardened portions hit against the legs and other body regions of a wearer and cause pain at the hit body regions.

Accordingly, a principal object of the present invention is to provide an underpants type disposable diaper in which hardened portions are decreased at the joined sections to prevent pain of a wearer who is in wearing of the diaper or who has the diaper on, and fusing stability is particularly improved at manufacture of the diaper.

Means to Solve the Problem

The present invention to solve the foregoing problem is as follows:

An underpants type disposable diaper having a front body part and a back body part which are joined at sides, thereby to form a waist opening and a pair of right and left leg openings, wherein
joined sections at sides of the front body part and back body part are formed with a large number of unit fusing portions arranged at uniform intervals, provided with groups each having continuous unit fusing portions of the same height, and divided into segments according to the groups of unit fusing portions of different heights The underpants type disposable diaper according to an embodiment, wherein the joined sections are each divided into an upper segment and a lower segment in a direction from a side end of the waist opening to a side end of the leg opening, the segments are different in height of unit fusing portions positioned therein with a relationship: (the height of thermally fusing portions positioned in the upper segment)>(the height of thermally fusing portions positioned in the lower segment).

The underpants type disposable diaper according to an embodiment, wherein the upper segment and the lower segment are different in number of laminated sheets with a relationship: (number of laminated sheets of the upper segment)>(number of laminated sheets of the lower segment).

The underpants type disposable diaper according to embodiments, wherein a ratio of distance between the upper segment and the lower segment is 1 to 3:1 to 2.

The underpants type disposable diaper according to any one of the embodiments, wherein height of unit fusing portions in the upper segment is 0.5 to 5 mm, and height of unit fusing portions in the lower segment is 0.1 to 2 mm.

The underpants type disposable diaper wherein
the joined sections are each divided into four segments: a waist segment; an upper side segment; an intermediate side segment; and a lower side segment, in a direction from a side end of the waist opening to a side end of the leg opening, and
the segments have a relationship in number of laminated sheets and height of unit fusing portions: (those of the upper side segment)>(those of the waist segment) (those of the intermediate side segment)>(those of the lower side segment).

The underpants type disposable diaper, wherein a ratio of distance among the waist segment, the upper side segment, the intermediate side segment, and the lower side segment is 4 to 6:2 to 4:20 to 24:5 to 7.

The underpants type disposable diaper, wherein height of the unit fusing portion is 0.3 to 3 mm in the waist segment, 0.5 to 5 mm in the upper side segment, 0.3 to 3 mm in the intermediate side segment, and 0.1 to 2 mm in the lower side segment.

The underpants type disposable diaper according to any one of the embodiments, wherein the joined section has a width of 7 to 10 mm and a length of 100 to 350 mm.

The underpants type disposable diaper according to any one of the embodiments, wherein intervals between the unit fusing portions are 0.1 to 5 mm.

The underpants type disposable diaper according to any one of the embodiments, wherein the joined section has a joint strength ranging from 2.0 to 5.0 kg/50 mm.

Effect of the Invention

According to the present invention, it is possible to provide an underpants type disposable diaper that decreases hardened portions in the joined sections and eliminates a cause of pain brought to a wearer who is in wearing of the diaper or who has the diaper on.

In addition, the diaper has unit fusing portions arranged at equal intervals therebetween, which realizes fusing with a stable thermal conductivity.

This makes it possible to adjust the diaper in firmness while providing a desired adhesion force, by changing height of the unit fusing portions.

Incidentally, the present invention refers to a unit fusing portion as a single fusing portion in a fusing section where fusing portions and non-fusing portions are alternately arranged. In addition, a group of unit fusing portions constitutes a sequence of continuous unit fusing portions of the same height.

BRIEF DESCRIPTION OF NUMERALS

AB ... absorber, F ... front body part, B ... back body part, WO ... waist opening, LO ... leg opening, 1 ... liquid permeable top sheet, 2 ... liquid impermeable back sheet, 3 ... absorbent core, 5 ... outermost sheet, 5i ... folded portion, 6 ... holding sheet, 7 ... under-waist elastic member, 8 ... waist elastic member, 9 ... around-leg elastic member, 11 ... leak prevention sheet, 20 ... barrier cuff, 21 ... barrier sheet, 30 ... side edge joined section, S1 ... waist segment, S2 ... upper side segment, S3 ... intermediate side segment, S4 ... lower side segment, S5 ... upper segment, S6 ... lower segment, M ... unit thermal fusing portion, Mh ... height of a unit thermal fusing portion, Mw ... width of a unit thermal fusing portion, P ... interval between unit fusing portions, Z1 ... underpants type disposable diaper

BEST MODE FOR CARRYING OUT THE INVENTION

The present invention will be further described below in detail with regard to embodiments shown in the drawings.
<Basic Configuration as an Example of an Underpants Type Disposable Diaper According to the Present Invention>

Figure 1:
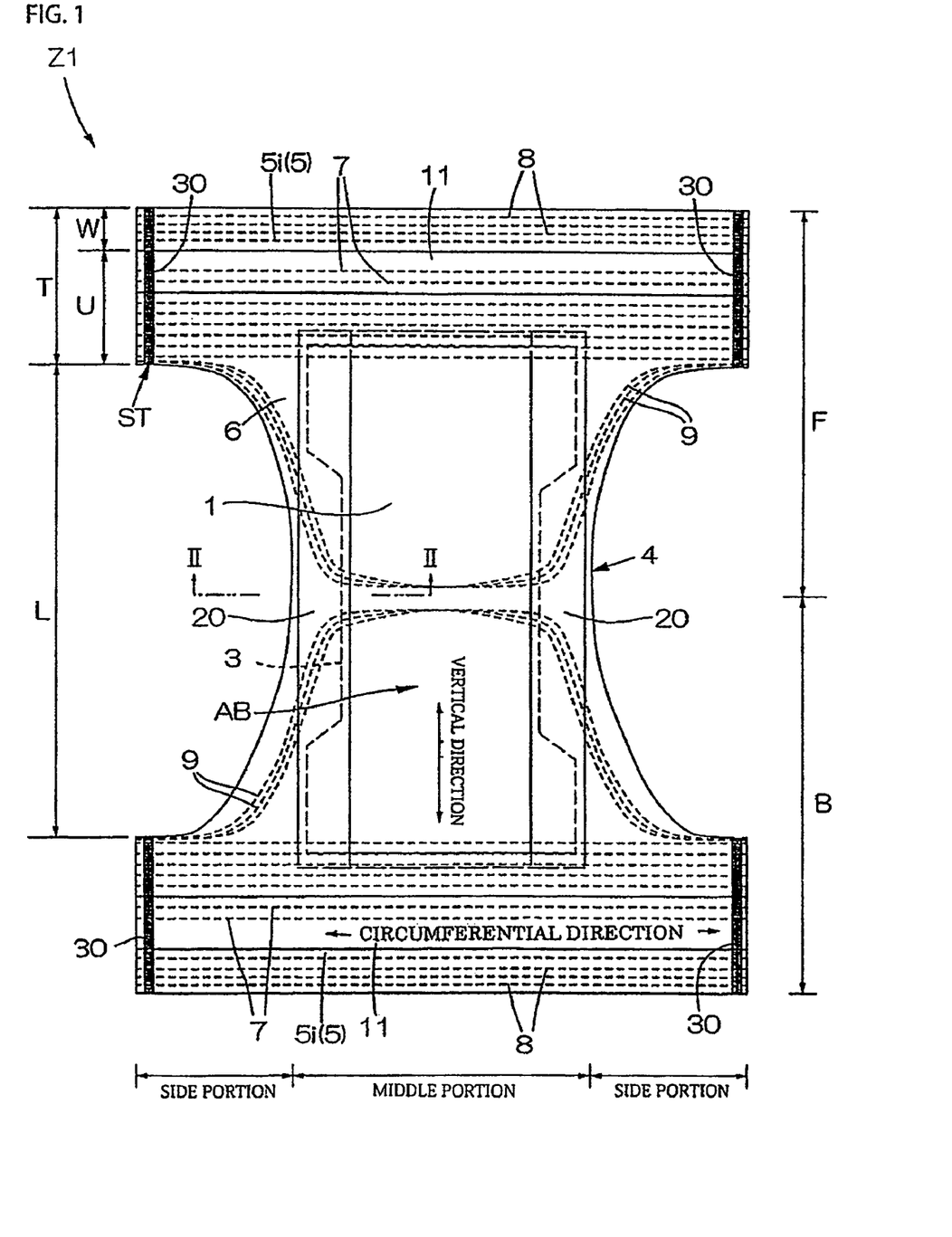
FIG. 1 is a development view of an inner side of an underpants type disposable diaper as an example.
Figure 2:
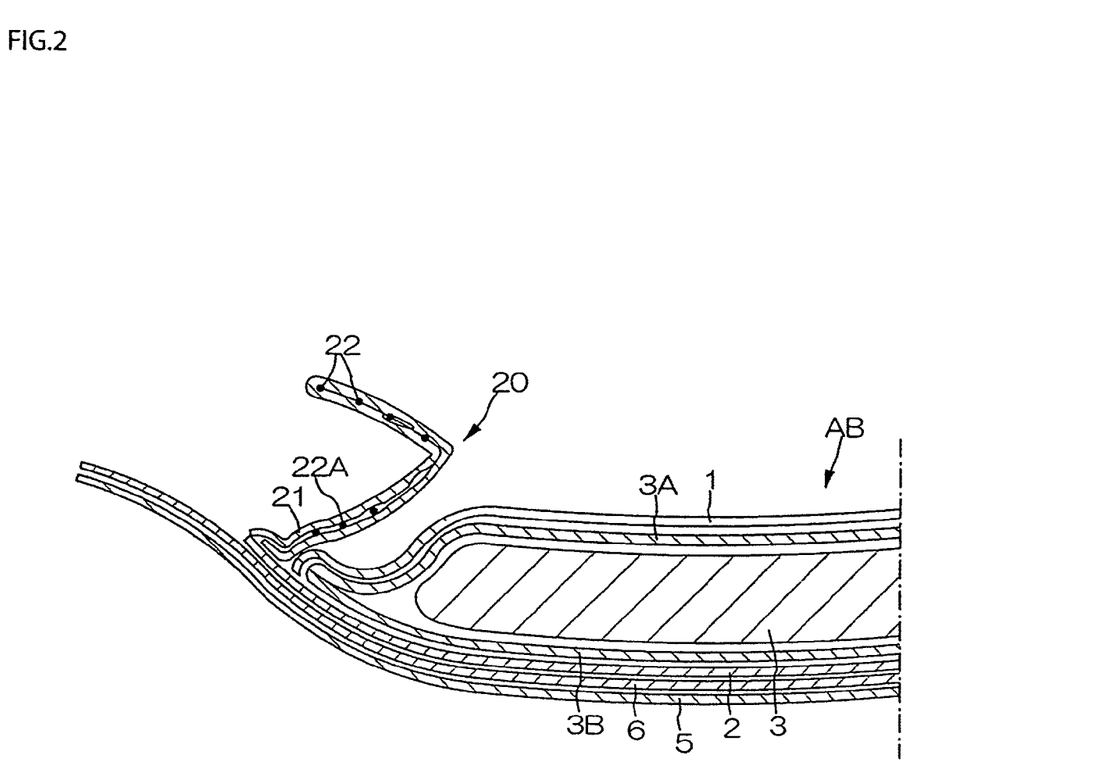
FIG. 2 is a view taken in a direction of allows along a line II-II in FIG. 1.
Figure 3:
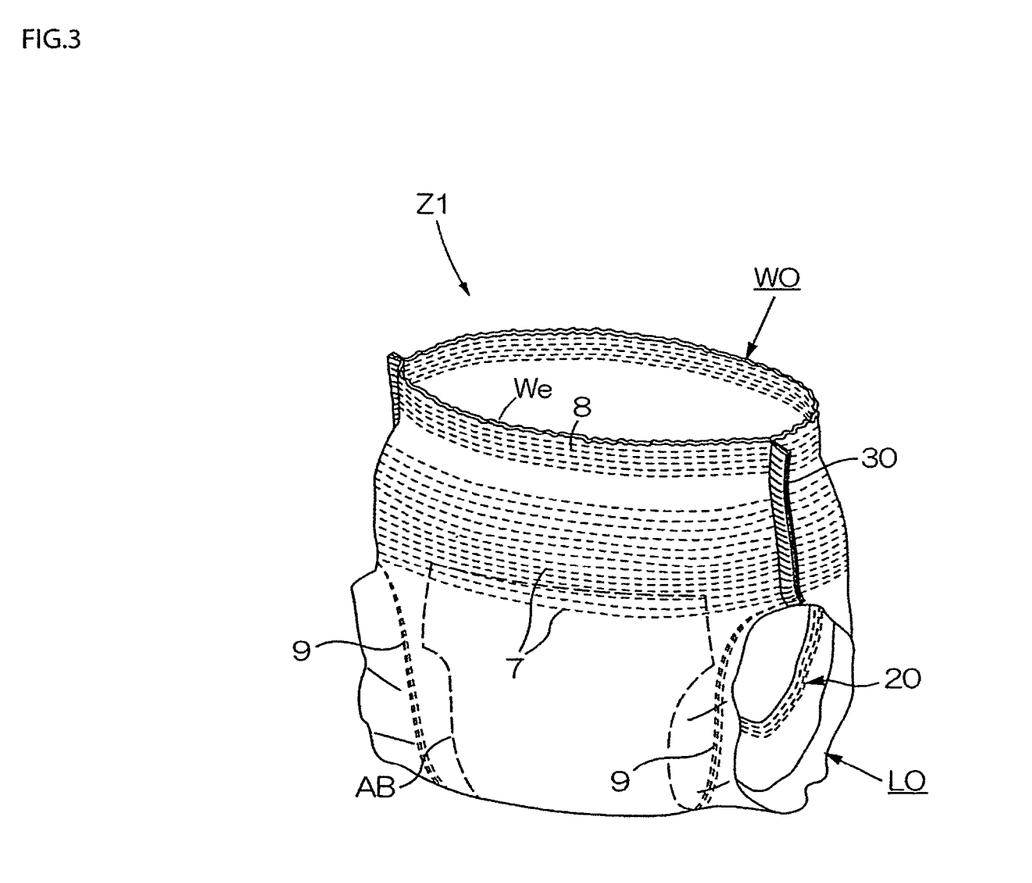
FIG. 3 is a frontal perspective view of the example of the underpants type disposable diaper.
Figure 4:
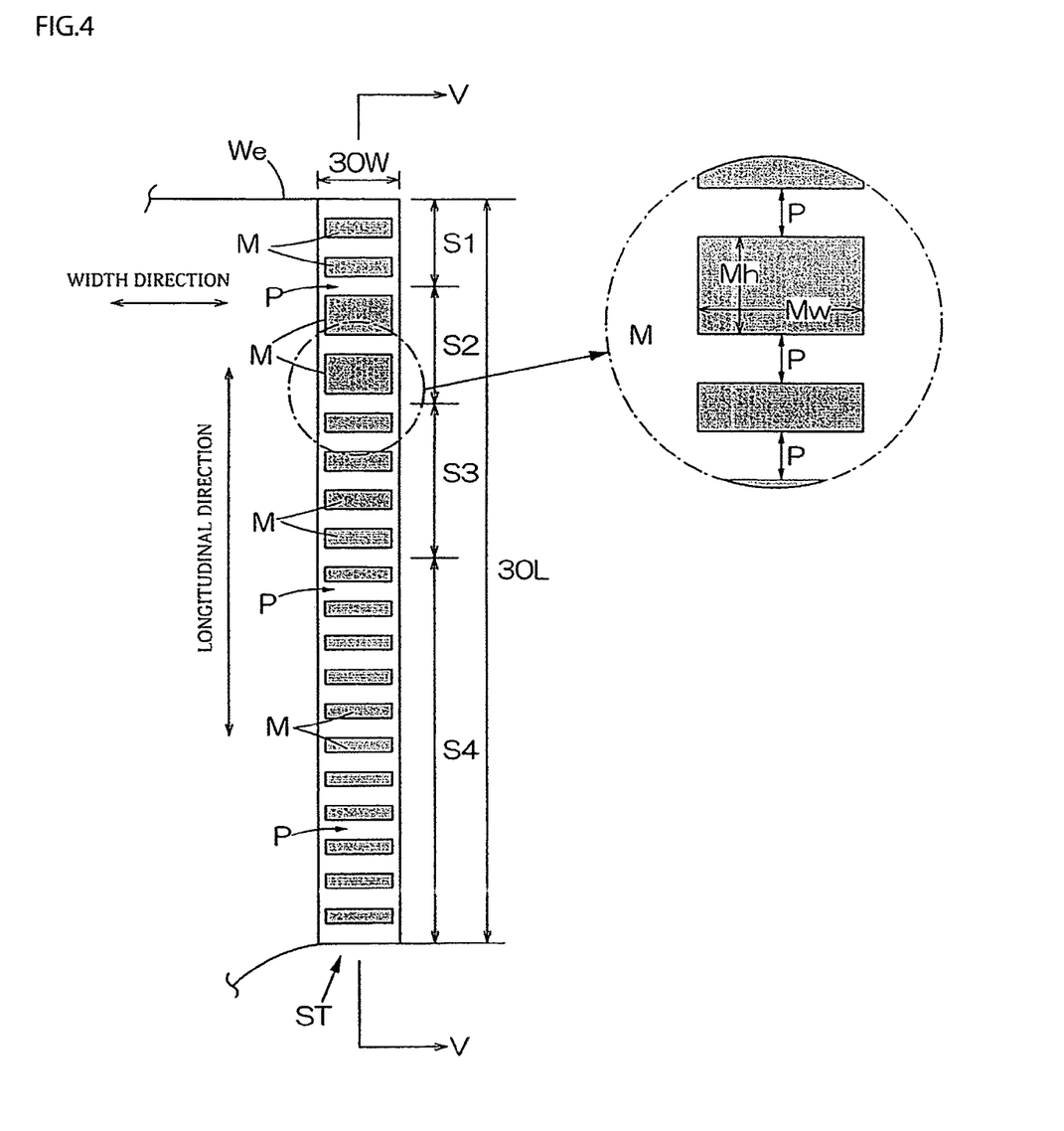
FIG. 4 is an enlarged front view of a joined section.
Figure 5:
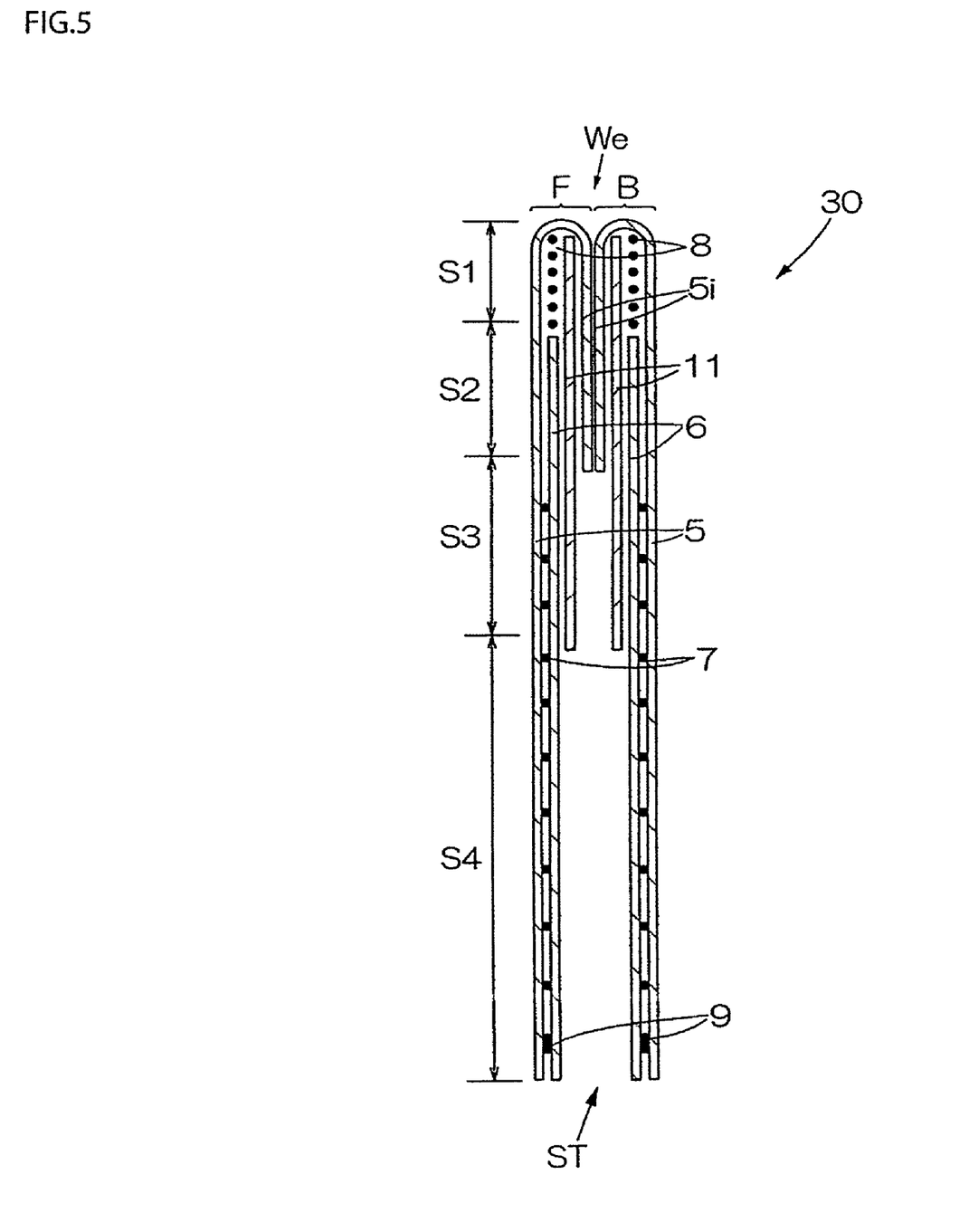
FIG. 5 is a view taken in a direction of allows along a line V-V in FIG. 4.

FIG. 1 shows an example of an underpants type disposable diaper in an opened state, FIG. 2 is a view taken in a direction of arrows along a line II-II in FIG. 1, and FIG. 3 is a schematic perspective view of a product. FIG. 4 is an enlarged view of a joined section, and FIG. 5 is a view taken in a direction of arrows along a line V-V in FIG. 4.

Designations of parts of the diaper will be described with reference to FIG. 1. First, a "vertical direction" refers to a direction in which a ventral side and a back side are linked, and a "circumferential direction" refers to a direction orthogonal to the vertical direction (or a direction of a product width). As shown in FIG. 3, a "waist opening edge" means an edge of the waist opening WO, and a "leg opening edge" refers to an edge of the leg opening LO. A "leg opening starting end" refers to a position where the leg opening edge of the leg opening LO and a joined potion 30 cross each other, which indicates a starting point of the leg opening edge. An "around-waist area T" refers to an entire area of a length covering from the waist opening edge to the leg opening starting end. The around-waist area T can be conceptually divided into a "waist section" W and an "under-waist section" U. The waist section W is 30 to 70 mm long, and the under-waist section U is 45 to 220 mm long in the vertical direction, although these lengths depend on a product size. A "crotch area" L refers to an area constituting the leg openings, more specifically, an entire area of a length covering from the leg opening starting end of the front body part to the leg opening starting end of the back body part. A "middle portion" refers to an intermediate area including a center line and excluding side portions of a product. The term "side portions" refer to portions on both sides of the around-waist area T.

Next, a structure of the disposable diaper in this embodiment will be described below. The disposable diaper includes main components as follows: an outermost sheet 5 constituting an outside of the diaper; a holding sheet 6 that is fixed to an inner surface of the outermost sheet 5 so as to cover the inner surface with the waist portion W excluded; an absorber AB that is fixed to an inner surface of the holding sheet 6 and extends in a front-back direction centering on the crotch portion 4 in a center of the diaper in the width direction; and front-back leak prevention sheets 11 that extend from front and back ends of the absorber AB to the waist portion W along an outline of the diaper.

Particularly in this embodiment, the back and ventral sides of the outermost sheet 5 are folded back to an innermost surface of the diaper at the waist opening WO, and folded portions 5i are fixed to an upper surface of the waist portion W in the leak prevention sheet. The folded portions 5i are desirably 30 to 70 mm in width in the vertical direction.

In addition, as is well-known, the disposable diaper has resilient and elastic members such as rubber threads arranged and fixed at appropriate positions, resulting in an increased fit to the body of a wearer. In this embodiment, as shown in FIG. 3, about five to ten waist elastic members 8 are arranged and fixed in an extended state circumferentially at the waist portion W between the outer portions and folded inner portions 5i of the outermost sheet 5 and between the outer portions of the outermost sheet 5 and the leak prevention sheet 6, at vertical intervals of about 1 to 10 mm therebetween. In addition, about five to fifteen under-waist elastic members 7 are arranged and fixed in an extended state circumferentially at the under-waist portion U between the outermost sheet 5 and the holding sheet 6, at vertical intervals of about 5 to 15 mm therebetween, for an increased fit around the waist and prevention of urine from leaking in the front-back direction.

Further, about three to five around-leg elastic members 9 extend from one side edge 30 at both of the ventral and back sides, through one leg portion, the crotch portion 4, and the other leg portion, to the other side edge 30. The elastic members 9 are arranged and fixed between the outermost sheet 5 and the holding sheet 6, at no intervals therebetween in the side edges 30 and the crotch portion 4, and at intervals of 3 to 5 mm therebetween in the around-leg portion.

The foregoing sheets can be fixed to each other and the elastic members can be fixed to the sheets with the use of an adhesive agent such as a hot-melt adhesive.

Meanwhile, particularly as shown in FIG. 2, the absorber AB has a liquid permeable top sheet 1 that is made of a nonwoven fabric or the like, for example, and comes into direct contact with the skin of a wearer, a liquid impermeable back sheet 2 that is made of a plastic film of polyethylene or the like or a water-repellent nonwoven fabric, and an absorbent core 3 made mainly of fluff pulp that is enveloped by absorbent paper sheets 3A and 3B as necessary, and interposed between the foregoing two sheets. The absorber AB is formed by integrating the foregoing components and adhering them at a circumferential edge with a hot-melt adhesive or the like.

Further in this embodiment, as shown in FIG. 2, the absorber AB has around-leg barrier cuffs 20, 20 on both sides. The barrier cuffs 20 are each formed of a barrier sheet 21 that is folded back and doubled. A base end portion of an inner side of the barrier sheet 21 is fixed to the back sheet 2 with a hot-melt adhesive, and an extending portion of an outer side of the barrier sheet 21 is fixed to the main body back sheet 5 with a hot-melt adhesive or the like.

One or more leading end portion elastic members 22 made of belt-shaped rubber, thread rubber or the like, are fixed in an extended state around a folded free edge portion of the barrier sheet 21, with a hot-melt adhesive or the like. In addition, as shown in the drawing, the barrier cuffs 20 have each an outward portion that is formed by folding back a leading end outward at an almost middle portion of an erecting free section. One or more base end portion elastic members 22A are fixed in an extended state to an unfolded inward base end portion side (bottom side) with a hot-melt adhesive or the like.

In such a configuration, at a final stage of a diaper manufacturing process after manufacture of a half-finished product in an opened state shown in FIG. 1, the front body part F and the back body part B are entirely joined at edges on both sides in the longitudinal direction, by a fusing means such as ultrasonic sealing or thermal fusing (the joined section is designated by reference numeral 30), thereby to form the waist opening WO and the pair of right and left leg openings LO as shown in FIG. 3.

First Embodiment

As shown in FIG. 4, a disposable diaper Z1 of this embodiment in the foregoing basic configuration has a large number of square unit fusing portions M, M . . . arranged at uniform intervals P therebetween to form the joined section 30, according to the present invention.

The unit fusing portions M has each a height Mh in the longitudinal direction (vertical direction) and a width Mw in a direction of a product width.

With the foregoing sheet arrangement pattern, the joined section 30 can be divided conceptually depending on the number of laminated sheets, in a direction from the side end of the waist opening to the side end of the leg opening, into four segments: a waist segment S1; an upper side segment S2; an intermediate side segment S3; and a lower side segment S4.

More specifically, as is apparent from FIG. 5, each body part has total three laminated sheets: the outermost sheet 5; the folded portion 5i; and the leak prevention sheet 11 at the waist segment, total four laminated sheets: the outermost sheet 5; the folded portion 5i; the leak prevention sheet 11; and the holding sheet 6 at the upper side segment, total three laminated sheets: the outermost sheet 5; the leak prevention sheet 11; and the holding sheet 6 at the intermediate side segment, and total two laminated sheets: the outermost sheet 5; and the holding sheet 6 at the lower side segment.

In addition, this embodiment is configured in such a manner that the foregoing segments have a relationship in the height Mh of the unit fusing portion M: (that of the upper side segment S2)>(that of the waist segment S1)=(that of the intermediate side segment S3)>(that of the lower side segment S4), in accordance with the numbers of laminated sheets.

In this configuration, intervals P between the unit fusing portions M among the segments are made uniform as stated above. Specifically, intervals between unit fusing portions of different heights in different segments are all unified, and intervals between unit fusing portions of the same height in one segment are all unified.

As foregoing, by making differences in height Mh of the unit thermal fusing portion M among the segments, and unifying intervals P between the unit fusing portions, it is possible to adjust firmness (softness) appropriately for each segment while ensuring joint stability at the joined section 30.

A desired ratio of distance among the waist segment S1, the upper side segment S2, the intermediate side segment S3, and the lower side segment S4, is 4 to 6:2 to 4:20 to 24:5 to 7. With such a ratio, it is possible to ensure a preferred fit and provide a favorable feel of wearing due to decreased firmness around the legs.

The height Mh of the unit fusing portion M is desirably 0.3 to 3 mm in the waist segment, 0.5 to 5 mm in the upper side segment, 0.3 to 3 mm in the intermediate side segment, and 0.1 to 2 mm in the lower side segment. With such value ranges, it is possible to ensure a generally required joint strength and provide preferred firmness (softness) to each of the segments.

Second Embodiment

In the first embodiment, the joined sections 30 are each divided into segments in sorting by number of laminated sheets. However, in the present invention, the joined section 30 may not necessarily have such segments with different numbers of laminated sheets. Further, for example, it is possible that the joined sections 30 are each is divided into segments in consideration of total thickness or total firmness of laminated sheets, or the like before deciding the heights of the unit fusing portions to be arranged in thus determined joined sections 30.

Precisely, a second embodiment where there is no difference in number of laminated sheets of the joined sections 30 will be described below.

Figure 6:
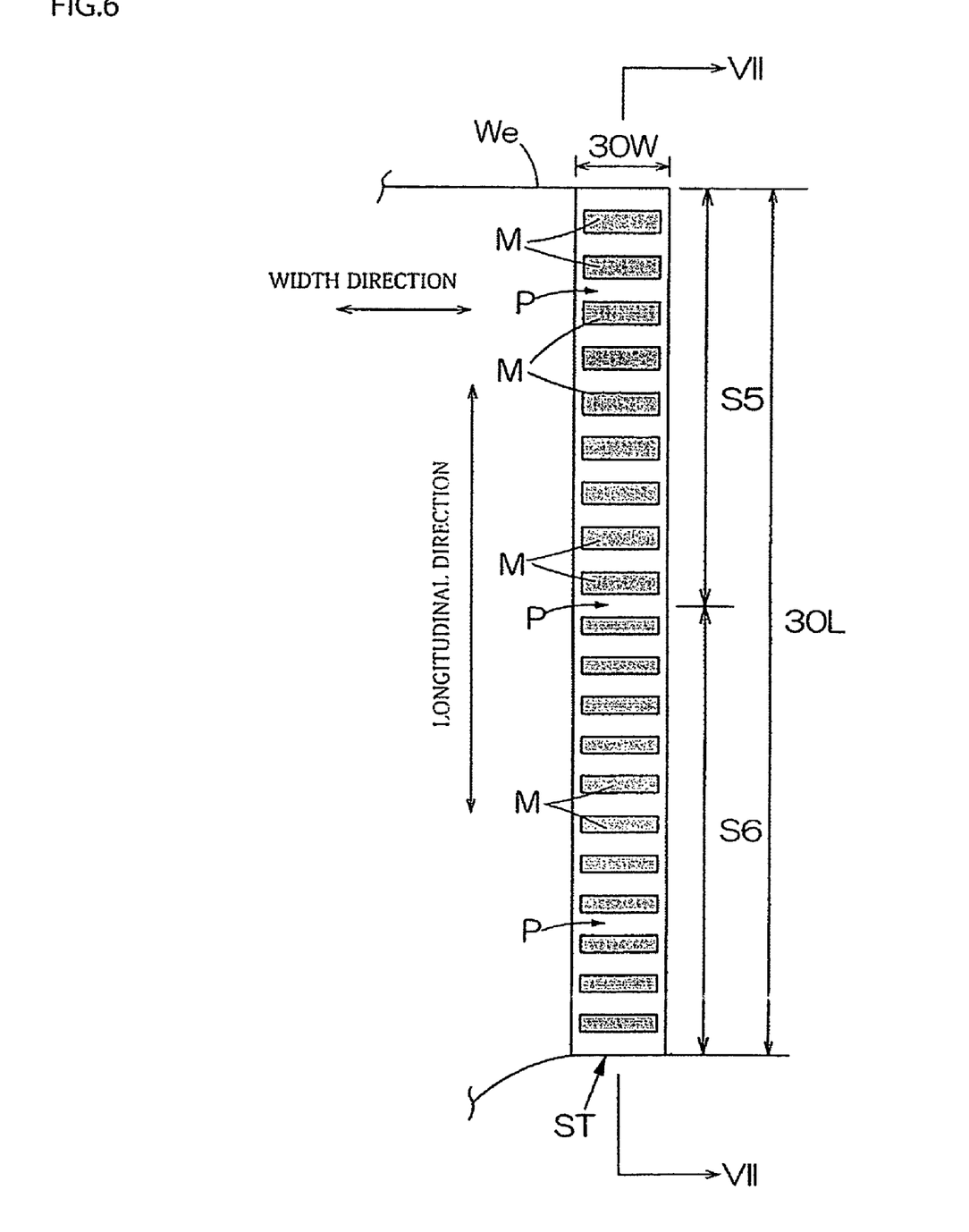
FIG. 6 is a front view of a joined section of a second embodiment.
Figure 7:
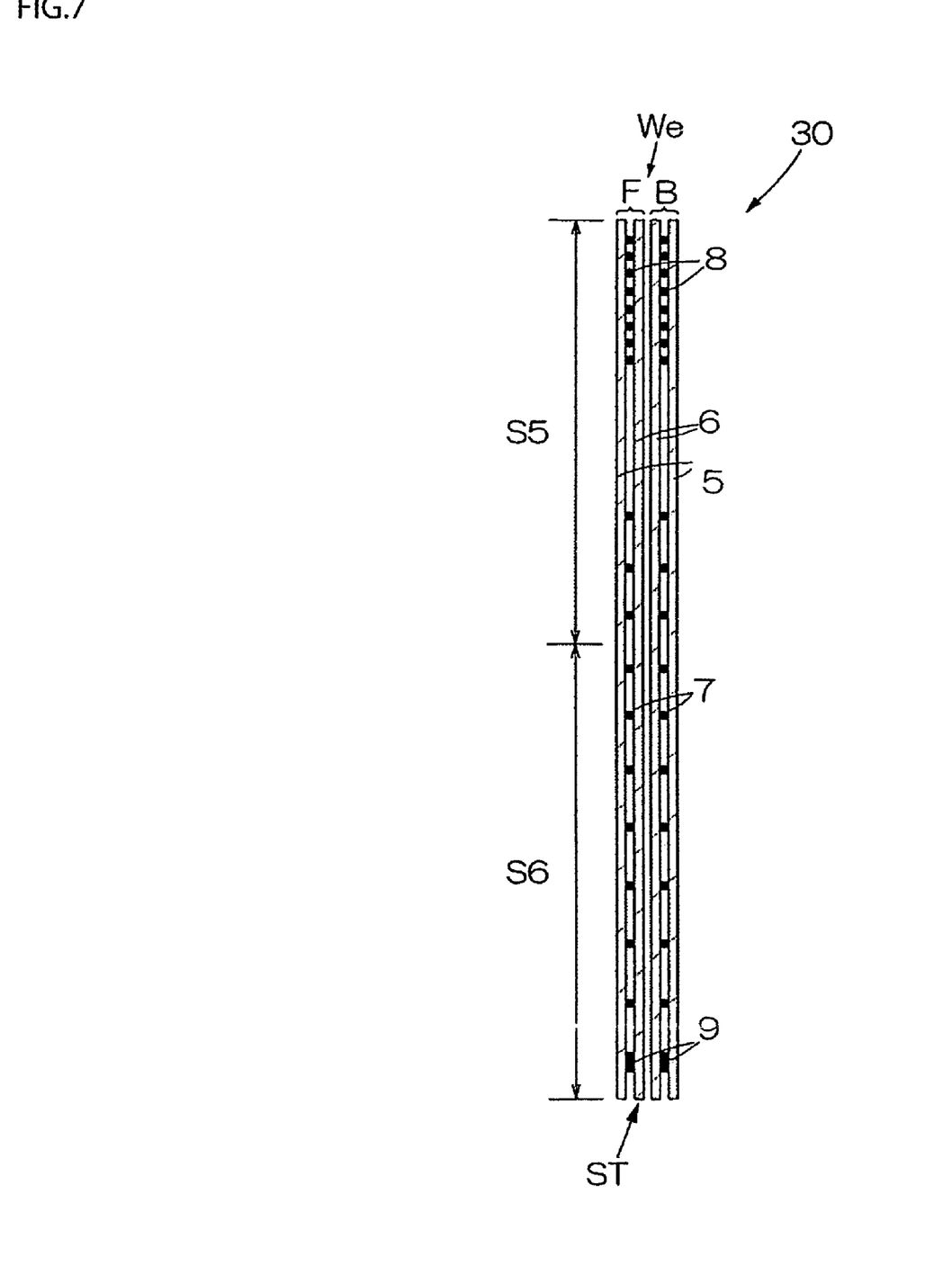
FIG. 7 is a cross-section view taken along VII-VII in FIG. 6.

FIG. 6 is a front view of the joined section 30 of this embodiment and FIG. 7 is a view taken in a direction of arrows along a line VII-VII in FIG. 6. As shown in these drawings, the disposable diaper of this embodiment is composed of only the outermost sheet 5 and the holding sheet 6 at least at the joined section 30. The outermost sheet 5 is not folded back at a waist opening edge We and there is no leak prevention sheet. That is to say, the joined section 30 has a two-layered structure in which the outermost sheet 5 and the holding sheet 6 are laminated through all the segments.

In such a layered structure, the joined sections 30 of this embodiment have each a large number of square fusing portions M, M . . . arranged at uniform intervals P therebetween in the longitudinal direction.

In addition, the joined sections 30 of the second embodiment are each arbitrarily divided into an upper segment S5 and a lower segment S6, in a direction from the waist opening side end to the leg opening side end. The segments have a relationship in heights Mh of the fusing portions M: (that of the upper segment S5)>(that of the lower segment S6). As a matter of course, the second embodiment is the same as the first embodiment, in that intervals between the unit fusing portions of different heights in different segments and intervals between the unit fusing portions of the same height in one segment, are all equal and set as uniform intervals P through the entire joined sections.

With such a relationship, the intervals P between the unit fusing portions M are uniform, and therefore the upper segment S5 and the lower segment S6 provide excellent fusing stability with little difference therebetween in ability of retaining adhesion by thermal fusing. In general, the leg opening starting end ST of the lower segment S6 comes into contact with the leg of a wearer and often causes firmness to the wearer. However, such problem will not occur in the present case, because the lower segment S6 is soft due to the relative small height Mh of the unit fusing portion M. On the other hand, the upper segment S5 is firm. Therefore, the diaper is excellent in fit and attachment properties.

A ratio of distance between the upper segment S5 and the lower segment S6 may be arbitrarily selected depending on size and shape of the diaper, and is desirably about 1 to 3:1 to 2.

In addition, if the joined sections 30 are each divided into the upper segment S5 and the lower segment S6, the height Mh of the unit fusing portions M in the upper segment S5 is preferably 0.5 to 5 mm, and the height Mh of the unit fusing portions M in the lower segment S6 is preferably 0.1 to 2 mm. With such value ranges, the diaper is improved in balance between softness and separation strength.

In other respects than the sheet lamination mode, e.g., arrangement mode of the absorber and resilient and elastic members, the configuration of the second embodiment is the same as the basic embodiment.

As a matter of course, this embodiment may be modified as appropriate such that the upper and lower segments have a relationship in number of laminated sheets of the joined sections: (that of the upper segment)>(that of the lower segment).

(Other Configurations)

In the present invention, regardless of the first or second embodiment, the joined sections have each desirably a width 30 W of 7 to 10 mm and a length of 100 to 350 mm. If the width 30 W of the joined section is less than 7 mm, it is difficult to obtain a desired joint force necessary for normal use. If the width 30 W exceeds 10 mm, it is difficult to provide softness even in accordance with the present invention.

In addition, a length 30L of the joined section is less than 100 mm, the diaper becomes deteriorated in fit and causes a higher possibility of leakage from the waist opening edge. On the other hand, if the length 30L is redundant in excess of 350 mm, it is difficult to attach or detach such diaper.

Further, the intervals P between the unit fusing portions are preferably 0.1 to 5 mm. With the intervals P of less than 0.1 mm, it is difficult to make differences in softness among the segments; even if the segments have the varying heights Mh of the unit fusing portions M. If the intervals P exceed 5 mm, the diaper causes a higher possibility of leakage of a body liquid from any non-fusing portion between the unit fusing portions.

Moreover, the joined sections 30 desirably range 2.0 to 5.0 kg/50 mm in joint strength. If the joint strength is less than 2.0 kg/50 mm, the diaper causes a possibility of being separated at the joined section(s) in normal use. If the joint strength exceeds 5.0 kg/50 mm, the diaper becomes difficult to tear and open at the joined sections at disposal or replacement.

The joint strength of the joined sections in the present invention can be measured in the following manner: (A) first, on each of the ventral and back sides of the diaper, portions 60 mm long in the circumferential direction by 50 mm wide are cut out from segments in the joined section 30, as test specimens; (B) then, each test specimen is set on a tensile tester while it is stretched in the circumferential direction of the diaper. At the time, the specimen is sandwiched and fixed, at its upper and lower ends each having 10 mm wide, between upper and lower chucks (not shown) of the tensile tester, respectively. The tensile tester is adjusted under conditions: a crosshead speed is 500 mm/min; and a distance between the chucks is 100 mm. Then, the tensile tester is operated to make a measurement until the joined section specimen is broken, and then a rupture point is read from a test result chart as the joint strength of the joined section.

In the present invention, preferable joint strength of the joined sections has been defined. It should be noted that, joint strength measured for any portion of the joined section always falls within the defined range of joint strength.

The joint strength of the joined sections can be adjusted by making appropriate changes to the kind, presence or absence, number, material, joint temperature or the like of the constituent elements of the joined sections 30 (for example, in the foregoing example, the outermost sheet 5, the holding sheet 6, the leak prevention sheet 11, the elastic members 7, 8, and 9, and an adhesive), thereby to produce an underpants type disposable diaper satisfying the requirements of the present invention. Such adjustment of the joint strength is naturally included in the scope of the present invention. For example, as is apparent from the embodiment, the joint strength can be raised by decreasing an amount of an adhesive to be used for attachment of the sheets at the joined sections.

The invention claimed is:

1. An underpants type disposable diaper having a front body part and a back body part which are joined at sides, thereby to form a waist opening and a pair of right and left leg openings, wherein
    joined sections at sides of the front body part and back body part are formed with a large number of unit fusing portions arranged at uniform intervals, in a longitudinal direction, provided with groups each having continuous unit fusing portions of the same height, and divided into segments according to the groups of unit fusing portions of different heights;
    the joined sections are each divided, in a direction from a side end of the waist opening to a side end of the leg opening, into four segments comprising a waist segment, an upper side segment, an intermediate side segment, and a lower side segment,
    the segments having a relationship with respect to the number of laminated sheets wherein the number of laminated sheets of the upper side segment is greater than the number of laminated sheets of the waist segment which is greater than or equal to the number of laminated sheets of the intermediate side segment which is greater than the number of laminated sheets of the lower side segment, and
    the segments having a relationship with respect to the height in the longitudinal direction of unit fusing portions wherein the height of unit fusing portions of the upper side segment is greater than the height of unit fusing portions of the waist segment which is greater than or equal to the height of unit fusing portions of the intermediate side segment which is greater than the height of unit fusing portions of the lower side segment.

2. The underpants type disposable diaper according to claim 1, wherein a ratio of distance among the waist segment, the upper side segment, the intermediate side segment, and the lower side segment is 4 to 6:2 to 4:20 to 24:5 to 7.

3. The underpants type disposable diaper according to claim 1, wherein the height of the unit fusing portion is 0.3 to 3 mm in the waist segment, 0.5 to 5 mm in the upper side segment, 0.3 to 3 mm in the intermediate side segment, and 0.1 to 2 mm in the lower side segment.

4. The underpants type disposable diaper according to any one of claims 1, 2 and 3, wherein the joined section has a width of 7 to 10 mm and a length of 100 to 350 mm.

5. The underpants type disposable diaper according to any one of claims 1, 2 and 3, wherein intervals between the unit fusing portions are 0.1 to 5 mm.

6. The underpants type disposable diaper according to any one of claims 1, 2 and 3, wherein the joined section has a joint strength ranging from 2.0 to 5.0 kg/50 mm.

7. The underpants type disposable diaper according to claim 1, wherein the diaper comprises:
- an outermost sheet constituting an outside of the diaper,
- a holding sheet that is fixed to an inner surface of the outermost sheet so as to cover the inner surface with the waist portion excluded,
- an absorber that is fixed to an inner surface of the holding sheet and extends in a front-back direction centering on a crotch portion of the diaper, and
- front-back leak prevention sheets that extend from front and back ends of the absorber to the waist portion;

longitudinal directional end portions of the outermost sheet are folded back to innermost surfaces of the diaper at the waist opening, and the resulted folded back portions are respectively fixed to upper surfaces of the waist portions of the leak prevention sheets;

the waist segment is formed by laminated three layers comprising the outermost sheet, one of the front-back leak prevention sheets and one of the folded back portions of the outermost sheet;

the upper side segment is formed by laminated four layers comprising the outermost sheet, one of the front-back leak prevention sheets, the holding sheet, and one of the folded back portions of the outermost sheet;

the intermediate side segment is formed by laminated three layers comprising the outermost sheet, one of the front-back leak prevention sheets and the holding sheet; and the lower side segment is formed by laminated two layers comprising the outermost sheet and the holding sheet.

8. The underpants type disposable diaper according to claim 1, wherein longitudinal directional intervals between unit fusing portions of different heights in different segments are all unified, and vertical directional intervals between unit fusing portions of the same height in one segment are all unified.

* * * * *